United States Patent

Gummesson et al.

[19]

[11] Patent Number: 4,585,552
[45] Date of Patent: Apr. 29, 1986

[54] SYSTEM FOR THE MEASUREMENT OF THE DIFFERENCE BETWEEN TWO FLUID FLOWS IN SEPARATE DUCTS

[75] Inventors: Bengt-Ake G. Gummesson, Bara; Bengt M. Holmberg, Bjarred; Sven A. Jonsson, Staffanstorp; Ulf K. Mattisson, Sandby, all of Sweden

[73] Assignee: Gambro Lundia AB, Sweden

[21] Appl. No.: 531,277

[22] Filed: Sep. 12, 1983

[30] Foreign Application Priority Data

Sep. 28, 1982 [SE] Sweden .............................. 8205529

[51] Int. Cl.⁴ ............................................. B01D 13/00
[52] U.S. Cl. ................................. 210/87; 210/321.3
[58] Field of Search ................. 604/29; 210/929, 87, 210/321.2, 321.3

[56] References Cited

U.S. PATENT DOCUMENTS

| 3,002,379 | 10/1961 | Hurley | 73/155 |
| 3,990,973 | 11/1976 | Boag et al. | 210/929 X |
| 4,486,303 | 12/1984 | Brous | 210/929 |

FOREIGN PATENT DOCUMENTS

| 614566 | 6/1935 | Fed. Rep. of Germany | 210/87 |
| 623889 | 1/1936 | Fed. Rep. of Germany | 210/87 |
| 1573007 | 6/1970 | Fed. Rep. of Germany | 210/87 |
| 1951378 | 4/1971 | Fed. Rep. of Germany | 210/87 |
| 3020756 | 12/1981 | Fed. Rep. of Germany | 604/29 |
| 1516315 | 1/1968 | France | 210/87 |
| 2056691A | 3/1981 | United Kingdom | 210/87 |
| 2003274B | 2/1982 | United Kingdom | 210/87 |

*Primary Examiner*—Frank Spear
*Attorney, Agent, or Firm*—Lerner, David, Littenberg, Krumholz & Mentlik

[57] ABSTRACT

A system for the measurement of the difference between two fluid flows in two separate ducts using one or more monitoring electrodes or the like arranged in respective ducts is disclosed. The fluid flow in one duct is adapted so that it is capable of being transferred to the other duct. This can be done, for example, using means for the alternate change-over of the fluid flows from their respective ducts to the opposite duct, so that ultimately all the electrodes and/or duct walls are acted upon to a substantially equal extent. Alternatively, this may be achieved using means for conducting one and the same fluid flow through both ducts where the fluid flow difference becomes zero and the measured value can be used as a new zero value for the continued measurement.

10 Claims, 3 Drawing Figures

SYSTEM FOR THE MEASUREMENT OF THE DIFFERENCE BETWEEN TWO FLUID FLOWS IN SEPARATE DUCTS

BACKGROUND OF THE INVENTION

The present invention relates in general to a system for the measurement of the difference between two fluid flows in two separate ducts using one or more monitoring electrodes or the like, arranged in respective ducts, and more particularly, to the measurement of relatively small differences between two relatively large fluid flows.

The present invention may also be applied, for example, to the measurement of ultrafiltration in a dialysis system, where the continuing clean dialysis solution flows through one duct, while the same solution, i.e., spent dialysis solution, but increased through ultrafiltration in the dialyser, flows through the other duct. The two main fluid flows may be in the order of magnitude of about 500 ml/min, whereas their difference, that is the ultrafiltration, may be in the range of about 0 to 40 ml/min and exceptionally a little higher.

In British Pat. No. 2 003 274 and in British Patent Application No. 2 056 691, two prior art systems for electromagnetic measurement of the differences between two fluid flows are described. In both systems, the fluid flows whose difference are to be measured pass through two parallel ducts. In accordance with the British patent, the measurement is performed using three electrodes which are acted upon as a function of the flowing medium and an externally applied magnetic field. In accordance with the British patent application, two main electrodes which cooperate with a number of earth electrodes are instead acted upon in the same manner.

Both prior art systems suffer from a number of notable disadvantages, namely that the flowing media acts upon the two ducts, or the electrodes, in a different manner. If, for example, such prior art systems are used for the measurement of ultrafiltration in dialysis, deposits from the contaminated liquid are often obtained on the electrodes and/or on the actual duct walls. Even a deposit in the order of magnitude of a few microns may cause substantial errors in the readings.

SUMMARY OF THE INVENTION

The present invention relates to a system for the measurement of the difference between two fluid flows in two separate ducts using one or more monitoring electrodes arranged in respective ducts. The above mentioned disadvantages of the prior art systems are solved in that the fluid flow in one duct is adapted so that it is capable of being transferred to the other duct. Means may be provided, for example, for the alternate change-over of fluid flows from their respective ducts to the opposite duct, so that ultimately all electrodes and/or ducts walls are acted upon to a substantially equal extent. This construction and arrangement of the system in accordance with the present invention has the advantage that the dialysis or any other continuing treatment can proceed without interruption.

Alternatively, means may be provided for the conducting of one and the same fluid flow through both ducts, where the difference in fluid flow becomes zero, and the then measured value can now be used as a new zero value or reference point for the continued measurement by the system.

When the last mentioned embodiment of the system is used for the measurement and possible control of fluid flow to and from a dialyser, such system is provided with means for the conducting of the clean dialysis solution through both of the ducts. At the same time, means can be provided for the by-passing of the fluid flow from the dialyser past the two ducts, thus allowing the dialysis to be continued, at least to a limited extent, during the zeroing or calibration while a clean-flushing of the contaminated ducts is achieved at the same time.

The present invention is used preferably in a system wherein the electrodes are arranged in a known manner in a magnetic field applied across the two ducts. Signals emitted from the electrodes are then picked up and used directly for the required adjustment in case of large differences between the fluid flows, while the difference in signals can be picked up and amplified for adjustment in the case of small differences between the fluid flows.

In accordance with one embodiment of the present invention, there is provided a system for measuring the difference in the rate of flow between two fluids. The system is constructed of a first duct having a first fluid flowing therethrough, a second duct having a second fluid flowing therethrough, measuring means for measuring the difference in the rate of flow between the first and second fluids within the first and second ducts, and transferring means for transferring the flow of the first fluid to the second duct.

Further in accordance with the above embodiment, the transferring means further includes transferring the flow of the second fluid to the first duct whereby the first and second ducts and the measuring means are effected by the first and second fluids substantially equally.

Still further in accordance with the above embodiment, the transferring means transfers the flow of the first fluid to within the second duct while maintaining the flow of the first fluid within the first duct such that the rate of flow of the first fluid through the first and second ducts is substantially equal, whereby the measured difference of the rate of flow of the first fluid flowing through the first and second ducts is adaptable as a reference for continued measurement.

BRIEF DESCRIPTION OF THE DRAWINGS

The above description, as well as further features and advantages of the present invention, will be more fully understood by reference to the following detailed description of a presently preferred but nonetheless illustrative system for the measurement of the difference between two fluid flows in separate ducts in accordance with the present invention when taken in conjunction with the accompanying drawings, wherein.

DETAILED DESCRIPTION

Figure 1:
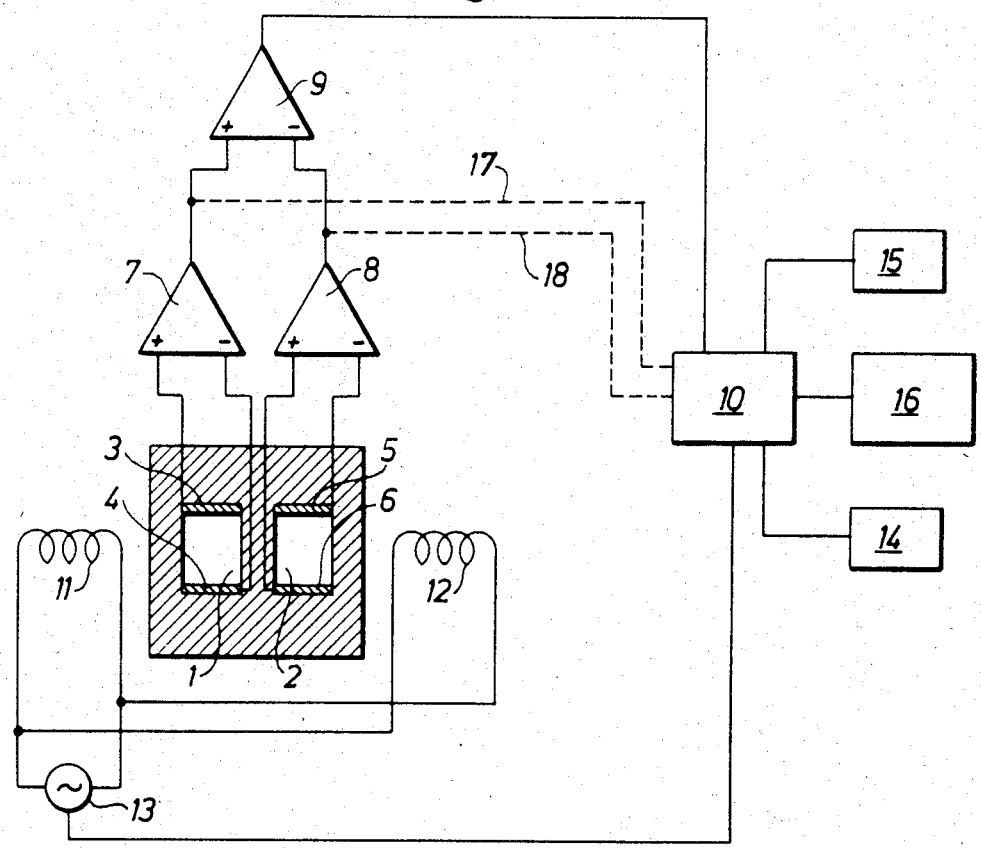
FIG. 1 shows schematically a block diagram of a preferred embodiment of the system in accordance with the present invention.

In FIG. 1, there is shown two ducts 1 and 2 having four electrodes 3, 4, 5 and 6 which are connected to differential measuring instruments 7 and 8, respectively, which are in turn connected to a differential measuring instrument 9. All differential measuring instruments 7, 8 and 9 are connected to a microcomputer 10. The fluid flows in the two ducts 1 and 2 are subjected to a magnetic field generated using coils 11 and 12, operated by a source of current 13, which is in turn controlled by the microcomputer 10. There is shown schematically that the microcomputer 10 can be provided with a suitable display 14 and a controller 15. At the same time, the microcomputer 10 can be adapted so as to control one or more valves 16. In regard to the theories and calculations behind the measurements in accordance with the system of the present invention, reference is made to the aforementioned prior art British patent and application. In this connection, the broken lines 17 and 18 are intended to indicate that the measured values obtained from the differential measuring instruments 7 and 8 are used directly for the control of the microcomputer 10 in the case of large differences between the fluid flows in the ducts 1 and 2. In the case of small differences between the fluid flows, the difference obtained from the differential measuring instrument 9 is used instead for the control of the microcomputer 10. The system may be provided for this purpose with different types of amplifiers, rectifiers, earth electrodes and other electric components which are known to those skilled in the art.

Figure 2:
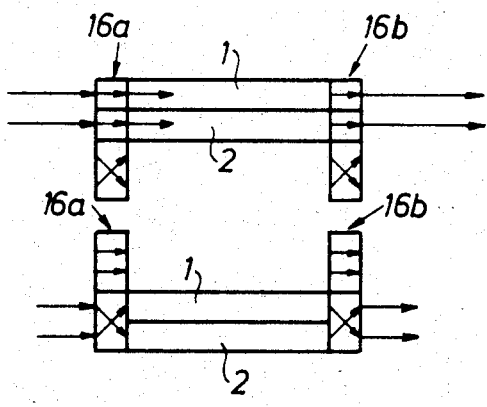
FIGS. 2 and 3 show schematically alternative embodiments of the connection for two parallel fluid flows whose difference in flow rate is measured using the system in accordance with the present invention.

In FIG. 1, the ducts 1 and 2 are shown in a cross-section transversely to the direction of fluid flow. In FIG. 2, the corresponding ducts 1 and 2 are shown instead in their longitudinal direction. Ducts 1 and 2 are combined with two valve blocks 16a and 16b by means of which the fluid flows from ducts 1 and 2, respectively, can be changed over alternatively to the opposite duct, so that ultimately all electrodes and/or duct walls are acted upon to a substantially equal extent.

Figure 3:
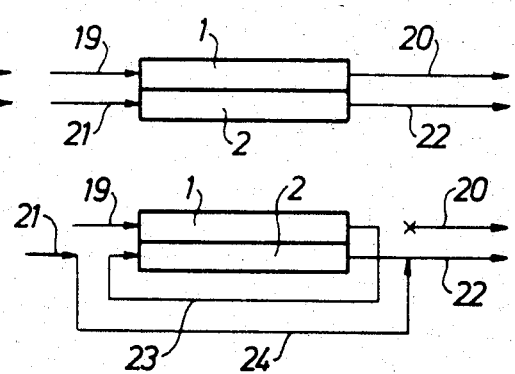

In FIG. 3, the ducts 1 and 2 are also shown in longitudinal direction. Use of the system in accordance with FIG. 3, for example, in dialysis, the arrow 19 designates the flow from a control unit normally used for dialysis. The arrow 20 designates the flow to the actual dialyser and the arrow 21 the flow from the dialyser. The arrow 22 designates the flow to a drain and/or to a possible regeneration and recirculation unit. In the bottom part of FIG. 3, the arrow 23 indicates how the clean dialysis solution can be conducted first through duct 1 and then through duct 2 so as to be removed finally to a drain or the like without passing the dialyser. At the same time, the arrow 24 indicates how the fluid flow from the dialyser, i.e., spent dialysis solution, can be conducted, past the two ducts 1 and 2, and directly to the drain. The embodiment of the system in accordance with FIG. 3 has the advantage over the embodiment of the system in accordance with FIG. 2 in that there is no risk of any particles broken loose from a previously contaminated duct being passed to the dialyser. In accordance with this embodiment of the system, any contaminations broken off are instead passed directly to the drain.

Accordingly, the present invention is not intended to be limited simply to the preferred embodiment described above, but can be varied within the scope of the following claims. The present invention is also applicable, for example, to systems with more or fewer electrodes. Likewise, it is not necessary to have parallel flow, but the system can also be adapted to counter-current flow. Finally, the calibration in accordance with the embodiment of the system shown in FIG. 3 can be repeated more or less frequently at regular intervals. In the case of dialysis, it has been found to be appropriate to calibrate once every half hour. The calibration may proceed in such a manner that the fluid flow difference is measured 300-400 times in a minute, whereupon a mean value is calculated which is substantially independent of any background noise.

What is claimed is:

1. In dialysis equipment including a dialyser, a system for measuring the difference in the rate of flow between first and second fluid streams, said first fluid stream comprising clean dialysis solution flowing to the dialyser and said second fluid stream comprising spent dialysis solution flowing from the dialyser, said system comprising a first duct for receiving said first fluid stream flowing therethrough, a second duct for receiving said second fluid stream flowing therethrough, measuring means for measuring the difference in the rate of flow between said first and second fluid streams within said first and second ducts, and transferring means for preventing the flow of said second fluid stream through said second duct while flowing said first fluid stream through both said first and second ducts without passing said first fluid stream through the dialyser and without altering said rate of flow of said first fluid stream between said first and second ducts such that said rate of flow of said first fluid stream through said first and second ducts is substantially equal, whereby the measured difference of the rate of flow of said first fluid stream flowing through said first and second ducts is adaptable as a reference.

2. The system of claim 1 wherein said transferring means transfers said clean dialysis solution from said dialyser through said first and second ducts.

3. The system of claim 2 further including by-pass means for by-passing the flow of said spent dialysis solution from said dialyser past said first and second ducts, whereby said dialysis operation may be continued during the flow of said clean dialysis solution through said first and second ducts.

4. The system of claim 1 wherein said measuring means includes a pair of electrodes arranged within said first and second ducts in a magnetic field, whereby large measured differences in the rate of flow between said first and second fluid streams can be used directly for adjustment by said system.

5. The system of claim 4 further including amplifying means for amplifying small measured differences between the rate of flow of said first and second fluid streams for use in adjustment by said system.

6. A system for measuring the difference in the rate of flow between first and second fluid streams, said first fluid stream comprising a relatively clean fluid stream and said second fluid stream comprising said first fluid stream and an added contaminant stream therein, said system comprising a first duct for receiving said first fluid stream flowing therethrough, a second duct for receiving said second fluid stream flowing therethrough, measuring means for measuring the difference in the rate of flow between said first and second fluid streams within said first and second ducts, and transferring means for transferring the flow of said first fluid stream to said second duct and for transferring the flow of said second fluid stream to said first duct, whereby said first and second ducts and said measuring means can be affected by said first and second fluid streams substantially equally.

7. The system to claim 6 wherein said measuring means includes a pair of electrodes arranged within said first and second ducts in a magnetic field, whereby large measured differences in the rate of flow between said first and second fluid streams can be used directly for adjustment by said system.

8. The system of claim 7 further including amplifying means for amplifying small measured differences between the rate of flow of said first and second fluid streams for use in adjustment by said system.

9. A system for measuring the difference in the rate of flow between first and second fluid streams, said first fluid stream comprising a relatively clean fluid stream and said second fluid stream comprising said first fluid stream and an added contaminant stream therein, said system comprising a first duct for receiving said first fluid stream flowing therethrough, a second duct for receiving said second fluid stream flowing therethrough, measuring means for measuring the difference in the rate of flow between said first and second fluid streams within said first and second ducts, and transferring means for preventing the flow of said second fluid stream through said second duct while transferring the flow of said first fluid stream through said second duct while maintaining the flow of said first fluid stream within said first duct such that the rate of flow of said first fluid stream through said first and second ducts is substantially equal, whereby the measured difference of the rate of flow of said first fluid stream flowing through said first and second ducts is adaptable as a reference.

10. The system of claim 9 further including a dialyser, wherein said first fluid stream comprises clean dialysis solution flowing therethrough and said second fluid stream comprises spent dialysis solution flowing therethrough, said dialyser adapted for use in a dialysis operation.

* * * * *